United States Patent
Van Roermund (10) Patent No.: US 11,058,897 B2
(45) Date of Patent: Jul. 13, 2021

(54) SYSTEM AND METHOD FOR DETECTING HARDWARE DEGRADATION IN A RADIATION THERAPY SYSTEM

(71) Applicant: Ion Beam Applications S.A., Louvain-la-Neuve (BE)

(72) Inventor: Raphael Van Roermund, Jerusalem (IL)

(73) Assignee: Ion Beam Applications S.A., Louvain-la-Neuve (BE)

( * ) Notice: Subject to any disclaimer, the term of this patent is extended or adjusted under 35 U.S.C. 154(b) by 39 days.

(21) Appl. No.: 16/606,121

(22) PCT Filed: Apr. 19, 2018

(86) PCT No.: PCT/EP2018/059999
§ 371 (c)(1),
(2) Date: Oct. 17, 2019

(87) PCT Pub. No.: WO2018/193022
PCT Pub. Date: Oct. 25, 2018

(65) Prior Publication Data
US 2020/0047003 A1    Feb. 13, 2020

(30) Foreign Application Priority Data

Apr. 19, 2017 (EP) ..................... 17167003

(51) Int. Cl.
*G01D 18/00* (2006.01)
*A61N 5/10* (2006.01)

(52) U.S. Cl.
CPC ................. *A61N 5/1075* (2013.01)

(58) Field of Classification Search
CPC .................................................. A61N 5/1075
See application file for complete search history.

(56) References Cited

U.S. PATENT DOCUMENTS

| 6,502,018 B1 | 12/2002 | Bessler |
| 2012/0314844 A1 | 12/2012 | Wiggers |

(Continued)

FOREIGN PATENT DOCUMENTS

| JP | 9-99110 | 4/1997 |
| JP | 11-161327 | 6/1999 |

(Continued)

OTHER PUBLICATIONS

International Search Report dated May 23, 2018, in corresponding International Application No. PCT/EP2018/059999; 4 pages.

(Continued)

*Primary Examiner* — Kiho Kim
(74) *Attorney, Agent, or Firm* — Finnegan, Henderson, Farabow, Garrett & Dunner LLP (57) ABSTRACT

An electron accelerator including a resonant cavity, an electron source, an RF system, and at least one magnet unit is provided. The resonant cavity further includes a hollow closed conductor and the electron source is configured to radially inject a beam of electrons into the cavity. The RF system is configured to generate an electric field to accelerate the electrons along radial trajectories. The at least one magnet unit further-includes a deflecting magnet configured to generate a magnetic field that deflects an electron beam emerging out of the resonant cavity along a first radial trajectory and redirects the electron beam into the resonant cavity along a second radial trajectory. The resonant cavity further includes a first half shell, a second half shell, and a central ring element.

18 Claims, 5 Drawing Sheets

(56) References Cited

U.S. PATENT DOCUMENTS

2013/0123565 A1* 5/2013 Denis ................. A61N 5/1048
600/1
2014/0061498 A1   3/2014 Honda et al.
2015/0126800 A1   5/2015 Kang et al.
2016/0321553 A1  11/2016 Marvasti et al.

FOREIGN PATENT DOCUMENTS

JP      2002-358120      12/2002
JP      2004-177167       6/2004
WO      WO-2010/044040    4/2010

OTHER PUBLICATIONS

Written Opinion of the International Searching Authority dated May 23, 2018, in corresponding International Application No. PCT/EP2018/059999; 6 pages.

* cited by examiner

SYSTEM AND METHOD FOR DETECTING HARDWARE DEGRADATION IN A RADIATION THERAPY SYSTEM

CROSS-REFERENCE TO RELATED PATENT APPLICATIONS

This application is a continuation of International Application No. PCT/EP2018/059999, filed Apr. 19, 2018, which claims the benefit of European Application No. 17167003.7, filed Apr. 19, 2017, each of which is hereby incorporated by reference in its entirety.

FIELD OF THE INVENTION

The invention relates to system and method for detecting hardware degradation in a radiation therapy system. More in general, the invention relates to radiation therapy.

BACKGROUND TO THE INVENTION

The invention generally relates to radiation therapy. Radiation therapy is used in a number of cancer treatments. Radiation therapy includes treatment of the animal, e.g. human, body by e.g. X-rays or electron beams. Herein particle therapy, such as treatment of the animal, e.g. human, body using ion beams, such as proton beams and/or carbon ion beams, is also considered as radiation therapy.

The radiation therapy is applied using a radiation therapy system, such as an ion beam delivery system. For each of a plurality of patients a field is delivered. Normally the field is delivered to a patient over multiple radiation sessions, e.g. over multiple days. The portion of a field delivered during a radiation session is referred to as a fraction. Thus, the radiation therapy system delivers a plurality of fields (one or more fields for each patient) and for each field there are multiple fractions given (each patient comes back a multiple number of times to receive the same fraction).

The radiation therapy system includes many components such as a particle accelerator, a beam transport system, a gantry, a beam delivery system, a patient positioner, and an X-ray patient positioning verification system. The beam delivery system comprises a so-called nozzle that defines the treatment field and the nozzle can be either a passive scattering type of nozzle or a spot scanning type of nozzle. A spot scanning nozzle comprises one or more magnets to scan the particle beam over a target area. Malfunction in any of such components, or parts thereof, may render the radiation therapy system out of service. Down time means that patients cannot be treated. Therefore, malfunction preferably is prevented. However, malfunction of components of the radiation therapy system is in general difficult to predict. Therefore, preventive maintenance is often scheduled at certain time intervals with a direct hint that maintenance is actually required.

SUMMARY OF THE INVENTION

An object of the present invention is to overcome, or at least diminish, these drawbacks. More in general an object of the present invention is to provide an improved, or at least alternative, method and system for detecting hardware degradation in a radiation therapy system. More in general an object of the present invention is to provide an improved, or at least alternative, radiation therapy system.

According to an aspect is provided a device for detecting hardware degradation in a radiation therapy system arranged for delivering a plurality of fractions for a plurality of radiation fields. Thus a plurality of radiation fields may be delivered, and each radiation field may be delivered in a plurality of fractions of that radiation field. It will be appreciated that the fractions may belong to different treatments. Within a single treatment the fractions may be substantially identical. The device includes a measurement unit arranged for measuring, for each fraction of the plurality of radiation fields, a value for one or more quantities representative of a functioning of one or more hardware components of the system. The device includes a normalizer arranged for, for each of the one or more quantities, normalizing the measured values. The device includes an averaging unit arranged for, for each of the one or more quantities, determining an average, e.g. a moving average, of the normalized values. The device includes a comparator arranged for, for each of the one or more quantities, comparing the average of the normalized values with a respective predetermined value. It will be appreciated that the predetermined value can be preset or automatically computed. The normalization allows that measurements of a quantity relating to a different fraction, e.g. a different field, layer or spot, can be used in the same statistical analysis, e.g. can be averaged, even though for instance setpoints or parameters may be different during the different fractions.

The normalizer can be arranged for normalizing, for each of the one or more quantities, the measured value taking into account values measured during delivery of previous fractions. Hence the normalization takes into account previous values, e.g. the whole history, of the quantity measured as delivered during previous fractions of the plurality of fields (e.g. of different patients). Thus, the normalizer can be arranged for normalizing, for each of the one or ore quantities, the measured value with respect to previous values, e.g. the whole history, of the quantity measured during delivery of previous fractions of the plurality of fields (e.g. of different patients). The normalizer can be arranged for normalizing, for each of the one or ore quantities, the measured value with respect to historical data of measured values. This normalization allows to, after the averaging, (e.g. on a daily basis) to establish a trend curve of the normalized, averaged measured values, e.g. over a long time period. The trend curve allows for assessing deviations from normal behaviour, e.g. (imminent) malfunction. Optionally, the normalizer is arranged for assigning a larger weight to values measured during delivery of more recent previous fractions than to values measured during delivery of older previous fractions. Optionally, the normalizer is arranged for normalizing, for each of the one or ore quantities, the measured value with respect to a predetermined number of previous values of the quantity.

The quantities representative of a functioning of a hardware component, can e.g. be a power consumption, an internal voltage, an internal current, a temperature, a vibration, an output power, an output quality, a noise component, etc. It will be appreciated that the quantities can relate to properties of the hardware component than can be used as diagnostic data for assessing a condition of the hardware component. Examples are 1) increase of the number of treatment pauses related to a drift on the signal of a given ionization chamber while redundant systems still follow the normal trend 2) variation in the beam position or shape related to a fluctuation in the output of a magnet power supply, etc.

Optionally, the device is arranged for monitoring the respective averages of the normalized values over a period of time. Hence changes over time can be detected.

Optionally, the comparator is arranged for determining, for each of the one or more quantities, whether the average of the normalized values displays a deviation from nominal behavior. Deviations from nominal behavior can e.g. be a drift, an oscillation and/or a jump in the average of the normalized values. Such deviation from nominal behavior can be an indication of degradation of a hardware component, or even imminent malfunction.

Optionally, the device is arranged for determining the predetermined value on the basis of a time development of the averages of the normalized values. Hence, a threshold for signaling deviation from nominal behavior can be determined from the time development of the average of the normalized values itself. Hence e.g. a nominal value for the average of the normalized values can be determined, e.g. during an initial period, and the threshold can e.g. be set at a predetermined deviation from the nominal value, e.g. 90% and 110%. Hence e.g. drifts, oscillations and/or jumps relative to the nominal value can be detected.

Optionally, the comparator stores and/or is arranged for retrieving information representative of a unique correlation between hardware degradation of a specific hardware component of the radiation therapy system and a deviation in the determined average of the normalized value for the associated quantity or quantities. Optionally, the device is arranged for determining a hardware degradation of a hardware component of the radiation therapy system on the basis of the determined average of the normalized value for one or more of the quantities, and on the basis of the unique correlation.

Optionally, the device includes a correlation unit arranged for receiving data representative of hardware degradation of one or more hardware components of the radiation therapy system, and for determining a unique correlation between hardware degradation of a specific hardware component and a deviation in the determined average of the normalized value for one or more quantities.

According to an aspect, degradations in the system performance are detected, and optionally a warning is triggered, before they lead to an equipment failure, and often a downtime. In order to achieve a useful detection of a variation in the system behavior, the quantities representative of a functioning of one or more hardware components of the system can be monitored. Optionally, such quantity is chosen such that it covers a single failure mode of a hardware component. Hence, a degradation on a given piece of hardware can be detected. Alternatively, or additionally, such quantity is chosen such that it is transparent to any other failure to the system. Alternatively, or additionally, such quantity is chosen such that it is a time invariant, meaning that the quantity remains constant over time under normal circumstances and does not depend on the nature of site activities (number of treatments, test fields, etc.).

Operations on a proton therapy center show a very interesting characteristic to detect such trends. Treatments include the delivery of a field. The field to be delivered is generally split into many substantially identical fractions that are delivered repetitively and often spread out over longer periods of time, e.g. each day over a period of one month. A fraction is generally composed of a plurality of layers, e.g. about 16 layers per fraction. A layer is generally composed of a plurality of spots, e.g. about 100 spots per layer. Also, generally many different treatments are given during one day, so that many different fields are delivered during a day. As different treatments are generally not synchronized, but start and end at different dates, fields, i.e. strings of substantially identical fractions (within one treatment), overlap with parts of other strings of substantially identical fractions (other treatments). This partial overlapping of different fields enables to extract data trends on each device in the system without modifying anything to site operations. For instance, there is no need to run specific fields at startup. Combining fields can greatly reduce the noise. Using parts of fields can further reduce noise, typically by a factor $\sqrt{30}$ ($\approx 5$) for quantities computed on each fraction, by a factor $\sqrt{500}$ ($\approx 20$) for quantities computed on each layer and a factor $\sqrt{5 \cdot 10^4}$ ($\approx 220$) for quantities computed on each spot.

The presented analysis is capable of detecting slow drifts in the system performance. Thereto data can be updated after each treatment. Fast degradations of a device (e.g. with an hour) are preferably managed by other means (errors, alarms, etc.).

Optionally, the device is a distributed device arranged for monitoring a radiation therapy system from a remote location. The remote location can e.g. be a monitoring center monitoring a plurality of radiation therapy systems, e.g. via a communications link, such as the internet.

Optionally, the device is arranged for detecting hardware degradation in a plurality of radiation therapy systems, such as mutually geographically remote radiation therapy systems.

Optionally, the one or more quantities are one or more of beam position (for spot scanning the beam is scanned over the target area by positioning the beam at various pre-planned positions), noise level in an ionization chamber (ionization chambers are used to measure the dose delivered to the patient or other ionization chambers are used to measure the position of the beam), or a time needed by a degrader to reach its position. When a passive scattering nozzle is used, a rotating modulation wheel can be used to modulate the energy of the beam, the one or more quantities can relate fluctuations of the wheel rotation.

According to an aspect is provided a monitoring system including one or more radiation therapy systems arranged for delivering a plurality of fractions for a plurality of, e.g. substantially identical, radiation fields and a device as described above.

According to an aspect is provided a method for detecting hardware degradation in a radiation therapy system delivering a plurality of fractions for a plurality of radiation fields. The method including the step of measuring, for each fraction of the plurality of radiation fields, a value for one or more quantities representative of a functioning of one or more hardware components of the system.

The method includes the step of normalizing, for each of the one or more quantities, the measured values. The method includes the step of determining, for each of the one or more quantities, an average of the normalized values. The method includes the step of comparing, for each of the one or more quantities, the average of the normalized values with a respective predetermined value.

Optionally, the step of normalizing includes, for each of the one or more quantities, normalizing the measured value taking into account values measured during delivery of previous fractions. Optionally, the step of normalizing includes, for each of the one or ore quantities, normalizing the measured value with respect to previous values, e.g. the whole history, of the quantity measured during delivery of previous fractions of the plurality of fields (e.g. of different patients). Optionally, the normalizing includes assigning a larger weight to values measured during delivery of more recent previous fractions than to values measured during delivery of older previous fractions.

Optionally, the method includes storing in a memory, for each of the one or more quantities, the determined average of the normalized values at subsequent points in time.

Optionally, the method includes the step of storing in the memory data representative of hardware degradation of one or more hardware components of the radiation therapy system. Optionally, the method includes the step of determining a unique correlation between hardware degradation of a selected hardware component and a deviation in the determined average of the normalized value for one or more quantities.

Optionally, the method includes the step of determining a hardware degradation of a hardware component of the radiation therapy system on the basis of the determined average of the normalized value for one or more of the quantities, and on the basis of a unique correlation between hardware degradation of said hardware component and a deviation in the determined average of the normalized value for said one or more quantities.

It will be appreciated that the method can be a computer implemented method.

According to an aspect is provided a computer program product for detecting hardware degradation in a radiation therapy system arranged for delivering a plurality of fractions for a plurality of radiation fields. The computer program product includes software code portions arranged for, when executed on a programmable apparatus, causing the apparatus to perform the steps of:

receiving, for each fraction of the plurality of radiation fields, a measured value for one or more quantities representative of a functioning of one or more hardware components of the system;

normalizing, for each of the one or more quantities, the measured values;

determining, for each of the one or more quantities, an, e.g. moving, average of the normalized values; and comparing, for each of the one or more quantities, the average of the normalized values with a respective predetermined value.

Optionally, the computer program product is included in a non-transitory data storage device.

It will be appreciated that any of the aspects, features and options described in view of the system apply equally to the method and computer program product. It will also be clear that any one or more of the above aspects, features and options can be combined.

BRIEF DESCRIPTION OF THE DRAWING

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawing.

DETAILED DESCRIPTION

Figure 1:
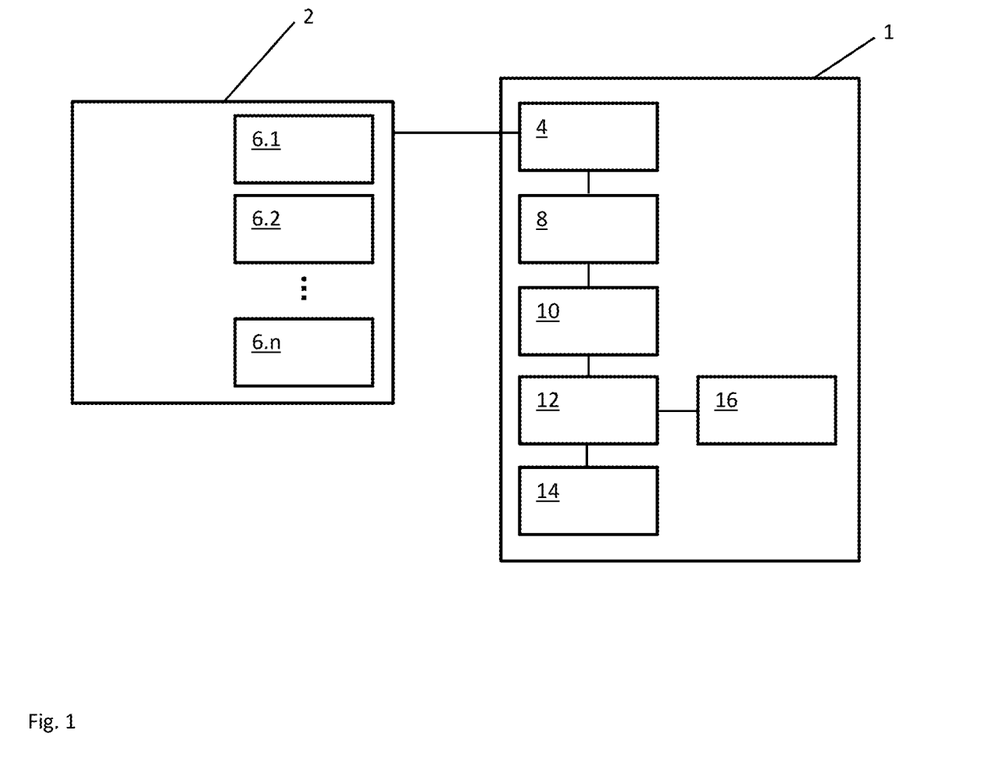
FIG. 1 shows an example of a device and a radiation therapy system.

FIG. 1 shows a schematic representation of a device 1 for detecting hardware degradation in a radiation therapy system 2. The radiation therapy system 2 is arranged for delivering a plurality of fractions for a plurality of radiation fields. In this example, a radiation treatment is delivered to a patient in a plurality of fractions over the course of several days. The radiation field of a fraction is composed of a plurality of layers. Each layer is composed of a plurality of spots.

The device 1 includes a measurement unit 4. The measurement unit 4 is arranged for measuring, for each fraction, a value for one or more quantities representative of a functioning of one or more hardware components $6.n$ (n=1, 2, 3, . . . ) of the system 2. Hardware components can be subject to malfunctioning. Herein a hardware malfunctioning can also be a degradation that is representative of an imminent breakdown, or indicative of a desired servicing or replacement. An aim is to predict hardware failure so that malfunctioning hardware components, or components about to malfunction, can be serviced, repaired or replaced before actual breakdown of the radiation therapy system 2. Examples of such hardware components can for instance be an ionization chamber (subject to degradation due to received cumulative dose), a modulation wheel (subject to mechanical wear i.a. dependent on the total number of cycles), electronic modules such as amplifiers, controllers etc. It will be appreciated that it is possible that the measurement unit 4 receives or retrieves measurement values from sensors, the sensors being part of the radiation therapy system 2. Hence, also malfunction and/or degradation of the sensors can be monitored using the device 1.

The device 1 includes a normalizer 8. The normalizer 8 is arranged for, for each of the one or more quantities, normalizing the measured values. The device 1 includes an averaging unit 10. The averaging unit 10 is arranged for, for each of the one or more quantities, determining an average, e.g. a moving average, of the normalized values. The device 1 includes a comparator 12. The comparator 12 is arranged for, for each of the one or more quantities, comparing the average of the normalized values with a respective predetermined value. The predetermined value can be preset or can be determined automatically.

Figure 2:
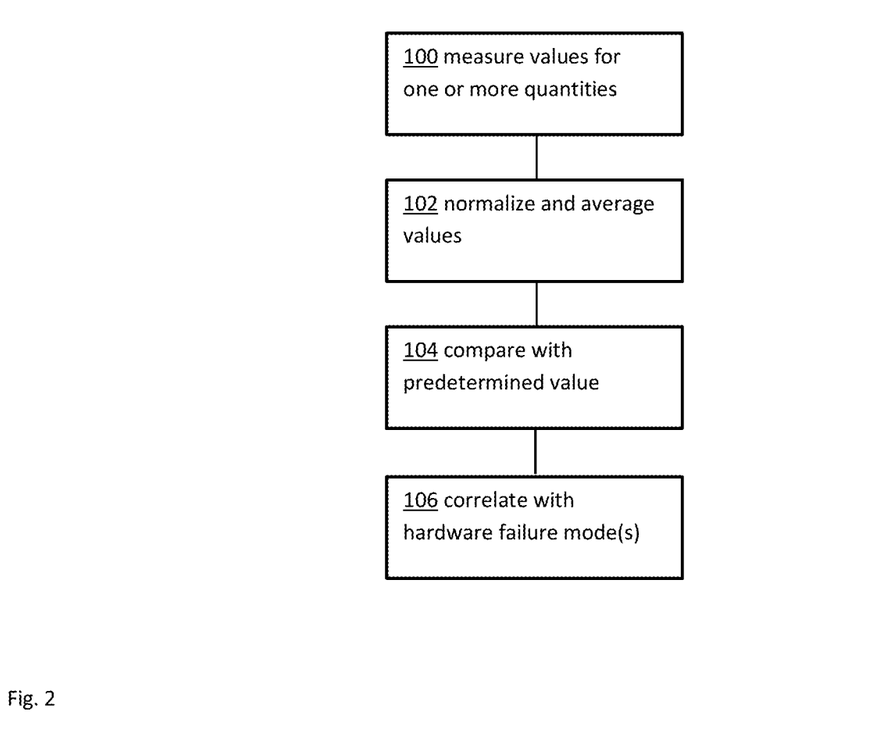
FIG. 2 shows an example of a flow chart.

The device 1 as explained thus far can be used as follows. FIG. 2 shows an exemplary flow chart.

In this example, it is considered that a number N of fields are delivered over a number M of days by the radiation therapy system 2. Here it is assumed that a fraction of each field is delivered once per day, however, it will be appreciated that it is also possible that a fraction of a field is delivered more or less than once per day. In this example a plurality of fractions of a plurality of fields is assessed, but it will be clear that similar applies for a plurality of layers, or a plurality of spots. The important point is the repeatability of the same element (fraction, layer, spot) over time.

The measurement unit 4 measures in step 100, for each field, a value for one or more quantities representative of a functioning of one or more hardware components. For each measured quantity is defined as the value of the quantity a for the field i on day j, or more in general the value of the quantity a for fraction j of field i. In the example quantities are considered having a strictly positive value (i.e. zero or larger), such as counts on an ionization chamber (IC).

Quantities that not always have a positive value, for instance a position, can be first transformed into a positive value. For simplicity a single quantity $a_{ij}$ is considered in this example.

The purpose of the method is to find the sequence $x_j$ that groups the information from all fields per day j. In this example the values of the measured quantity $a_{ij}$ for the fields i are normalized by the normalizer 8 and averaged by the averaging unit 10 in step 102 so that they contribute equally to normalized and, e.g. moving, averaged value $x_j$. Here, the first value of a quantity for a field will determine its normalization factor with respect to the mean of all other values for that quantity for all other fields on that day j.

The construction of the effective field $x_j$ on day j can be done as follows. A normalization factor $R_{ij}$ is defined such that $$R_{ij} = \sum_{j'=j_{0i}}^{j-1} \quad (j > j_{0i}) \qquad \text{EQ 1}$$

$$\tilde{a}_{ij} = \frac{a_{ij}}{R_{ij}} \quad (j > j_{0i}) \qquad \text{EQ 2}$$

$$x_j = \sqrt{\frac{1}{N_j} \sum_i \tilde{a}_{ij}^2} \qquad \text{EQ 3}$$

where $N_j$ is the number of non-zero fields at time j, and $j_{0i}$ is the start time of field i. The sum in equation EQ 3 is made over all non-zero normalized fields at time j. The normalization factor $R_{ij}$ for each field i at moment j is calculated such that the normalized measured quantity $\tilde{a}_{ij}$ approaches best $x_j$ over its whole history up to day j−1. Thus, normalization is performed with respect to previous values, e.g. the whole history, of the measured quantity.

It will be appreciated that the first values of the quantity of a field might not be perfectly normalized due to lack of history. This can have an impact on the accuracy of $x_j$, especially when fields do not last very long in time or when there are few of them. If required, several solutions can be applied to improve this. For example, the contribution of a quantity value $a_{ij}$ to $x_j$ can be delayed so that only quantity values of fields that have cumulated enough events contribute. For example, $x_j$ can be corrected iteratively. The values up to the oldest running value $a_{ij}$ can be recomputed with the last computed normalization factors $R_{ij}$. For example, a decay parameter can be added as described hereinbelow.

It is noted that in the above example, according to equation EQ 1 the normalization factor $R_{ij}$ depends on the whole history of the quantity value $a_{ij}$. Under some circumstances, this might smear out some drifts in case fields last for a very long time. In an alternative example it is possible to add a decay parameter $\lambda$.

$$a_{ij} = \lambda a_{ij} + (1-\lambda) a_{i,j-1} \quad (j > j_{0i}) \text{ with } a_{i,j_{0i}} = a_{i,j_{0i}} \qquad \text{EQ 4}$$

$$\chi_j = \lambda x_j + (1-\lambda) \chi_{j-1} \quad (j > j_{0i}) \text{ with } X_{j_{0i}} = x_{j_{0i}} \qquad \text{EQ 5}$$

$$R_{ij} = \frac{a_{i,j_{0i}}}{\chi_{j-1}} \quad (j > j_{0i}) \qquad \text{EQ 6}$$

$$\tilde{a}_{ij} = \frac{a_{ij}}{R_{ij}} \quad (j > j_{0i}) \qquad \text{EQ 7}$$

$$x_j = \sqrt{\frac{1}{N_j} \sum_i \tilde{a}_{ij}^2} \qquad \text{EQ 8}$$

where $a_{ij}$ (resp. $\chi_j$) represents a moving average of (resp. $x_j$) in which more weight is given to recent events. The parameter $\lambda$ is between 0 (long memory) and 1 (short memory). Its value can be chosen depending on a time constant of the drift under observation. It is also possible that normalization factor $R_{ij}$ depends on a partial history of the quantity value $a_{ij}$, e.g. the most recent six quantity values.

In the above examples it is assumed that the time between successive events can be considered as being constant. It will be clear that in practice this will not always be the case, e.g. due to lack of treatments during a week-end, a patient that has been rescheduled, etc. For example to account for non-constant time durations between events, $\lambda$ can be replaced by $\lambda^{\Delta t}$, where $\Delta t$ is the time between successive events, in equations EQ 4 and EQ 5. In case a given field has not been irradiated on a certain day the average drift of $x_j$ can be transferred to $a_{ij}$:

$$a_{ij} = a_{i,j-1} \frac{x_j}{x_{j-1}} \qquad \text{EQ 9}$$

It will be appreciated that in some cases, time might not be the best scale to observe degrading of components. It is possible to replace time by an alternative axis, such as a cumulative dose to study radiation damage, or a number of use cycles for a moving (e.g. rotating) part. The equations as described above remain valid.

Normalizing values under a sum introduces a bias. Fluctuations of +10% or −10% on $a_{ij}$ have an asymmetric impact on $x_j$ since $1/(1+10\%) \neq 1-10\%$. As a consequence, for large fluctuations, a slope could be observed on $x_j$ that is not related to a trend on the raw data $a_{ij}$. As an example, the case $\lambda=0$ is considered (normalization from the first value on the field). Naming $\sigma_j$ the standard deviation on field $a_j$, and from the Taylor series $$\frac{1}{1+x} = 1 - x + x^2 + O(x^3), \qquad \text{EQ 10}$$

we introduce a bias of the order $(\sigma_j/\bar{a}_j)^2$ on each new fraction. The slope observed on $x_j$ will be $$\frac{dx_j}{dt} = \left(\frac{\sigma_j}{\bar{a}_j}\right)^2 f + O\left(\frac{\sigma_j}{\bar{a}_j}\right)^3 \qquad \text{EQ 11}$$

where f is the frequency at which new fractions start. Exemplary methods to avoid, or at least reduce, this error are presented herein below.

A simple solution to reduce the artifact in EQ 11 is to reduce $\sigma_j/a_j$ by adding a constant value A to $a_{ij}$ ($a_{ij} \rightarrow a_{ij} + A$). This operation is preferably reverted at the end so that the amplitude of the fluctuations on $x_j$ is independent of A:

$$x_j \rightarrow (x_j - 1)\frac{A}{\bar{a}} + 1, \qquad \text{EQ 12}$$

where $\bar{a}$ is the average of all values $a_{ij}$.

A more elaborate way to eliminate, or at least reduce, the drift artifact is to correct the results by compensating for the error made in EQ 11. This can be done iteratively by calculating a and correcting $x_3$ until convergence is reached.

Now an example is described following EQ 1. Consider the following matrix with 3 fields as a function of time:

$$\begin{bmatrix} a_{11} & a_{12} & a_{13} & a_{14} & a_{15} & a_{16} & 0 & 0 & 0 \\ 0 & a_{22} & a_{23} & a_{24} & a_{25} & a_{26} & a_{27} & 0 & 0 \\ 0 & 0 & 0 & 0 & a_{35} & a_{36} & a_{37} & a_{38} & a_{39} \end{bmatrix}.$$

Herein the first row denotes the measured, non-zero, values $a_{ij}$ of the quantity for fractions of the first field (i=1), having measured values from days 1 through 6 (j=1 . . . 6). The second row denotes the measured, non-zero, values $a_{ij}$ of the quantity for fractions of the second field (i=2), having measured values from days 2 through 7 (j=2 . . . 7). The third row denotes the measured, non-zero, values $a_{ij}$ of the quantity for fractions of the third field (i=3), having measured values from days 5 through 9 (j=5 . . . 9). Similarly, the first column denotes the measured values for fractions of different fields on the first day (j=1), only the fraction of the first field (j=1) being non-zero in this example.

The first row (here denoting the first field) becomes the reference at day 1. The value $a_{11}$ can thus serve as the normalization factor for the first field:

$$\tilde{a}_{11} = \frac{a_{11}}{a_{11}} = 1 = x_1.$$

On the second day, the second field comes in and will be normalized to $x_2$. Thus, the measured quantities of the second day are normalized with respect to the measured quantity of the first day. Thereto $x_2$ is computed from the older fields (in this case the first field):

$$R_{12} = \frac{a_{11}}{x_1} = a_{11} \Rightarrow \tilde{a}_{12} = \frac{a_{12}}{a_{11}} = x_2. \qquad \text{EQ 13}$$

On the third day the first and second fields start contributing to $x_j$.

$$R_{13} = \frac{a_{11} + a_{12}}{x_1 + x_2} = \frac{a_{11} + a_{12}}{1 + \frac{a_{12}}{a_{11}}} = a_{11} \Rightarrow \tilde{a}_{13} = \frac{a_{13}}{R_{13}} = \frac{a_{13}}{a_{11}} \qquad \text{EQ 14}$$

$$R_{23} = \frac{a_{22}}{x_2} = a_{22}\frac{a_{11}}{a_{12}} \Rightarrow \tilde{a}_{23} = \frac{a_{23}}{R_{23}} = \frac{a_{23}}{a_{22}}\frac{a_{12}}{a_{11}} \qquad \text{EQ 15}$$

$$x_3 = \frac{1}{2}[\tilde{a}_{13} + \tilde{a}_{23}] = \frac{1}{2}\left[\frac{a_{13}}{a_{11}} + \frac{a_{23}}{a_{22}}\frac{a_{12}}{a_{11}}\right]. \qquad \text{EQ 16}$$

For the simplicity of the example, a linear sum has been taken rather than a quadratic one for $x_3$. Note that in this example $R_{12}=R_{13}$ because only one field contributed to $x_j$ before day three, in which case there is no reason to change the normalization. This will change on the next day as then both the first field and the second field have an impact on $x_3$.

The process goes on and $x_j$ will be such that it stands in the middle between $\tilde{a}_{1i}$ and $\tilde{a}_{2i}$. On the fifth day, the third field enters into action (is non-zero) and is normalized to $x_5$. It will start contributing to $x_j$ at day six.

Figure 3:
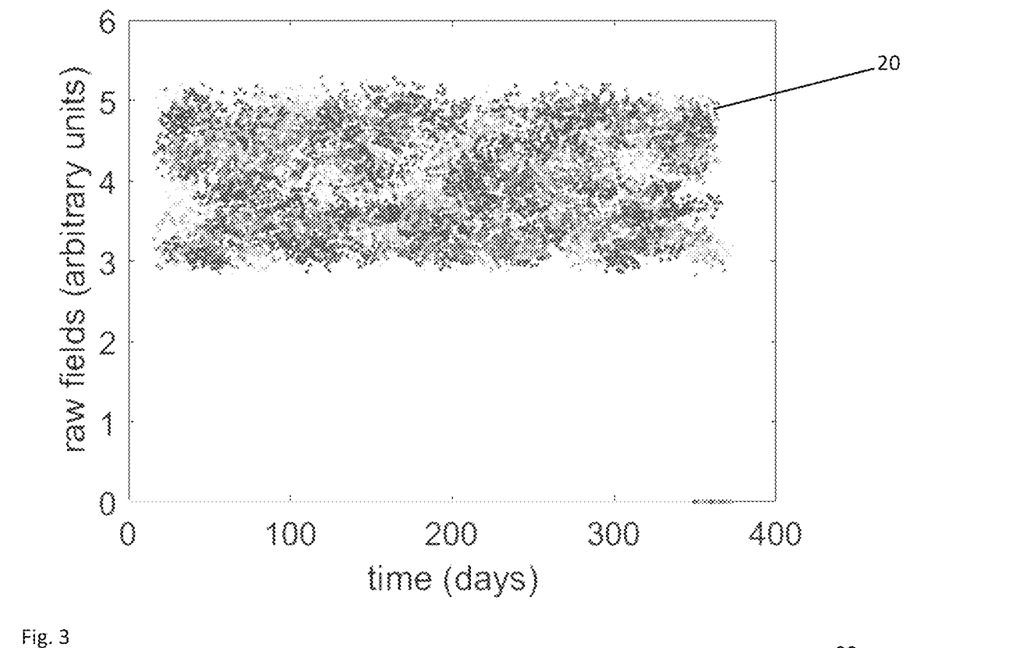
FIG. 3 shows an example of measured data.
Figure 4:
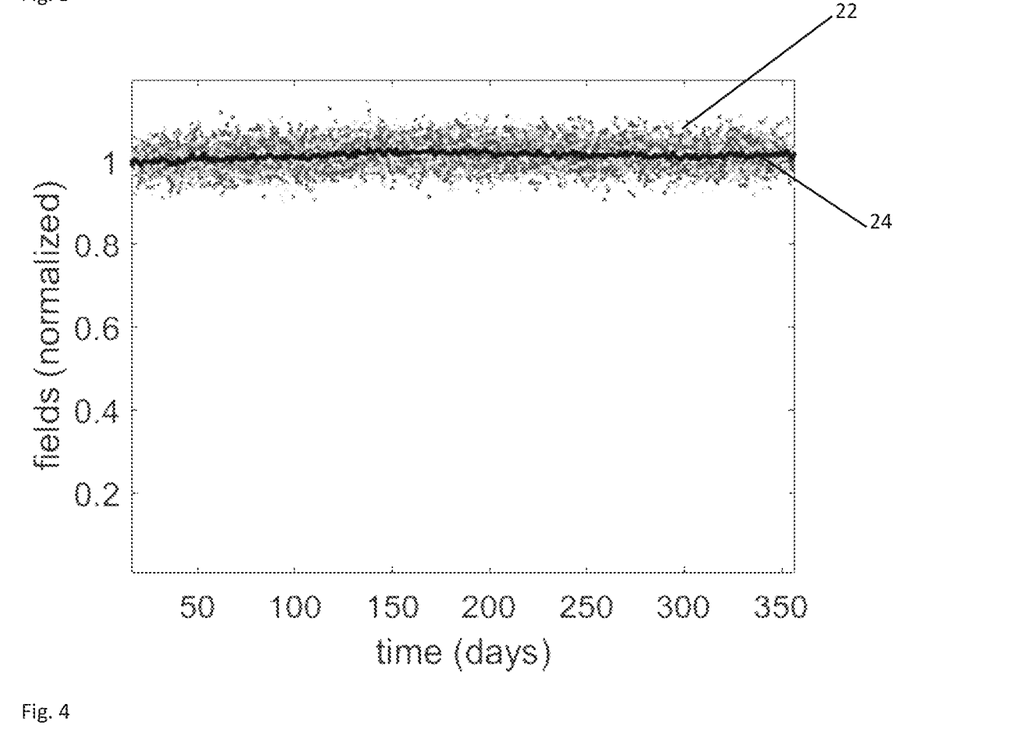
FIG. 4 shows an example of normalized data and normalized and averaged data.

Next is described a simulated experiment. For the experiment five hundred fields each including on average twenty fractions, i.e. ten thousand quantity values for fractions of fields, with random amplitude between 3 and 5 have been generated. Each field lasts for about twenty days, i.e. each field is delivered in fractions on twenty consecutive days substantially identically. The day to day fluctuations of the measured values are set to have a standard deviation of around 2.5%. This represents around one year of data for a treatment room with around thirty patients per day. FIG. 3 shows a points cloud 20 for the raw fields values $a_{ij}$, i.e. the raw values for the quantities measured in this experiment. In FIG. 4, fields values $a_{ij}$ have been normalized 22 to a same referential $\tilde{a}_{ij}$ and only the intrinsic fluctuations within each field are maintained. The normalization allows that measurements of a quantity relating to different fields, e.g. to different fractions, layers or spots of different fields, can be used in the same statistical analysis, e.g. can be averaged, even though setpoints or parameters may be different for the different fields. The black curve 24 shows the effective field $x_j$ built from the normalized fields $\tilde{a}_{ij}$. Single-field fluctuations are greatly reduced by averaging over all fields.

Figure 5:
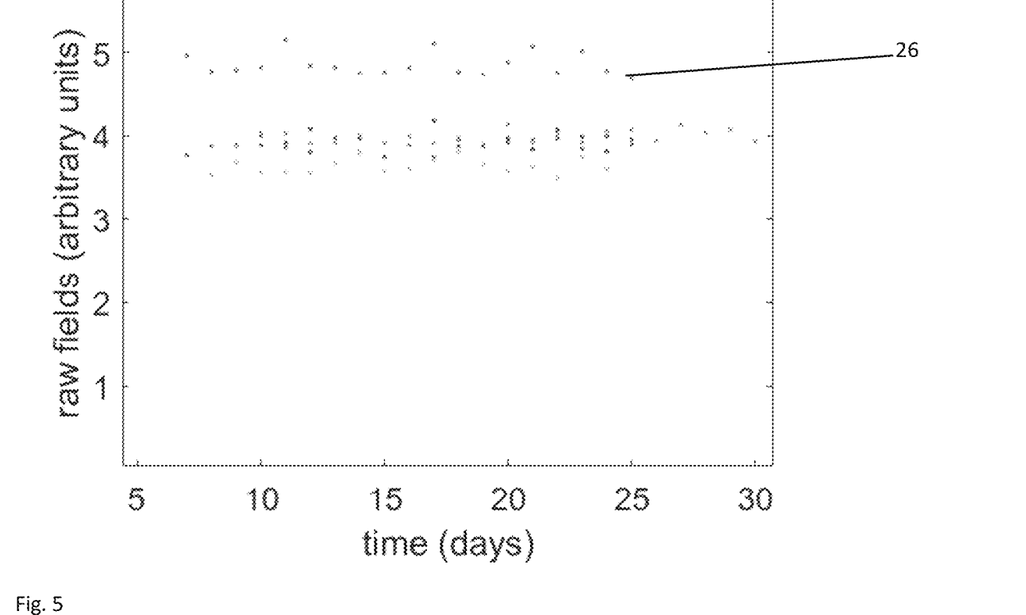
FIG. 5 shows an example of raw data.
Figure 6:
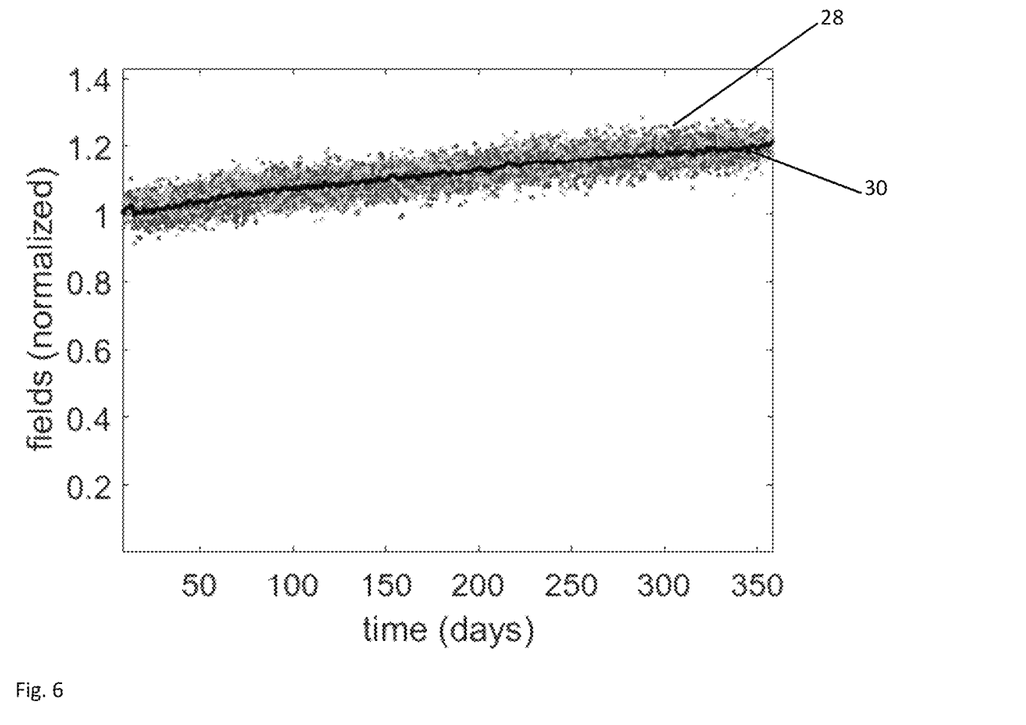
FIG. 6 shows an example of normalized data and normalized and averaged data.

In order to show the potential of the algorithm, a second experiment is simulated in which all fields undergo a small drift of 0.1% per day. FIG. 5 shows measured values 26 for five exemplary individual fields each extending over twenty days. As can be seen in FIG. 5, the drift of 0.1% per day is barely noticeable on the single fields because it is both a too short time period and a too noisy signal. FIG. 6 shows five hundred fields of about twenty fractions each, each field having a drift of 0.1% per day, normalized 28 as described above. Again the black line 30 represents $x_j$. It can be seen in FIG. 5 that by combining all five hundred fields together the impact of the 0.1% drift is clearly observable on $x_j$. The device 1 is arranged for monitoring the respective averages of the normalized values over a period of time. The comparator 12 is arranged for comparing in step 104 the average of the normalized values with a respective predetermined value. Here, the comparator is arranged for determining whether the average of the normalized values displays a deviation from normal behavior. In this example, the comparator 12 could take (a) historic value(s) of the normalized averaged value x, as a reference value. Alternatively, the comparator could take the value one (1) as reference value (here the values are normalized to one). In case the comparator 12 detects a deviation, e.g. $x_j<0.9$ or $x_j>1.1$, an alarm could be generated. Thereto, the device 1 can include a communications unit 16.

Sometimes, a field is be delivered more than once in a single day, for instance in case of patient quality assessment. This is an opportunity to reduce the noise by averaging the results inside $a_{ij}$.

Some fractions can be aborted, either by the system, or by the physicist. Although the remaining fractions of the field can be irradiated later on, such fields are preferably discarded to avoid unwanted noise on the data. A checksum on the actual number of delivered spots versus the intended number of spots can be used to automatically filter out these incomplete fields.

Fields that underwent a pause might add noise to the data while the pause has already warned the user that something went wrong with the system. It is possible to enable the user choose whether he wants to filter out such fields or not.

Hospitals sometimes modify the irradiation plan within the course of the treatment in order to deal with tumor shrinkage. The system can be arranged to automatically detect this, e.g. from a new patient ID, or by a checksum on the number of delivered spots and the total dose.

A regression in a new software release could result in a measured difference on a same patient when fractions overlap the time of the installation of the release. This provides an opportunity to detect potential changes pre and post release change. Preferably, the moment of the software release is flagged clearly to avoid confusion with a failure of a hardware component.

Figure 7:
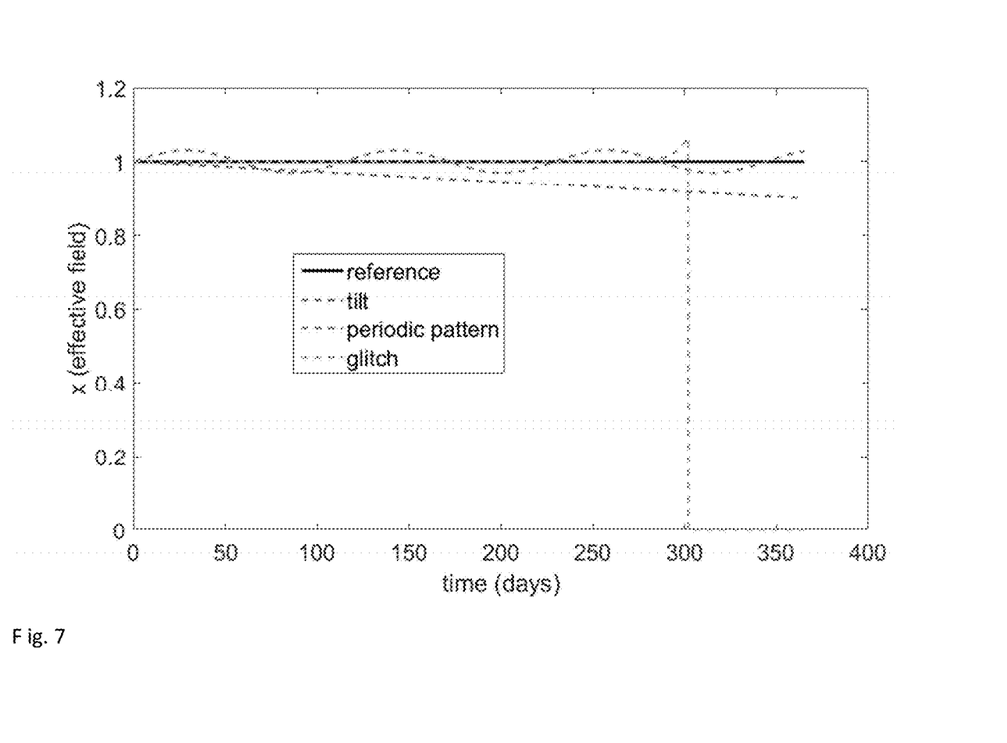
FIG. 7 shows examples of time curves.

Above it has been described how to create a reference variable that should remain constant under normal circumstances. The purpose is to detect when the system deviates out of normal behavior. FIG. 7 demonstrates a number of possible time behaviours of x, i.e. time sequences of $x_j$, that deviate from the expected constant value. A degradation or failure on a hardware component of the system could for example lead to a drift (blue curve). Alternatively, or additionally, the failure or degradation could lead to a periodic pattern (red curve). Alternatively, or additionally, the failure or degradation could lead to a fast change in the response (green). It will be common to observe drifts in the response of hardware signals, for instance on devices submitted to radiation damage or on magnetic Hall probes. Monitoring the slope of x over a long period of time should be able to detect this. A predetermined threshold can be defined (e.g. 20%). When the value of x crosses the predetermined threshold an alarm may be generated and/or maintenance can be planned. In view of the periodic patterns it is noted that these normally occur over very long time scales as the repeatability of data happens over days. Still, it can be insightful to investigate for periodic patterns in data, which could e.g. be related to the use of the system by the customer (variations in the number of treatments, difference between mornings and afternoons, impact of experimental missions, etc.) or other (humidity variations with seasons, etc.). For example a Fourier analysis can be used to extract such periodic patterns. In view of sudden changes, it is noted that "sudden" is relative as the effect relates to variations over days. Yet, some devices might show a change in their response without immediately preventing the system from operating, but such a change could be the first manifestation of further damage. For instance the decay parameter $\lambda$, and modification thereof, can enable a data analyst to extract information about such issues.

In the above example a single quantity a was measured and monitored. It will be appreciated that it is also possible to simultaneously measure and monitor a plurality of different quantities a, b, c, d, etc. According to an aspect, a dysfunctional hardware component can be identified independently of all other parts of the system and the use of the radiation therapy system. Thereto a set of quantities a, b, c, d, etc. can be monitored These quantities form diagnostic data that can be used as variables in identifying the defective, degrading, or otherwise dysfunctioning hardware component, or part thereof. The variables are chosen such that each hardware failure corresponds to a unique combination of variables. The variables are also chosen to be independent of the field properties (range, modulation, etc.). Preferably, the variables show as little noise as possible. Preferably, the variables do not average around zero, although this can be remedied as described hereinabove.

Figure 8:
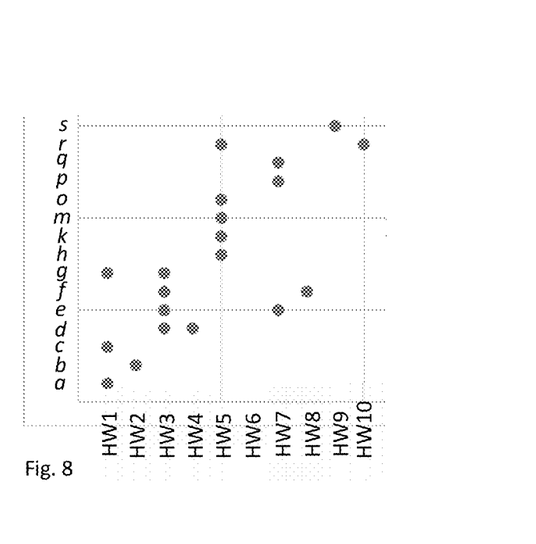
FIG. 8 shows an example of a matrix.

Two tables can be available. A first table can include all variables measured. A second table can include all identified hardware failures. A correlation matrix may be provided indicating correlation between the variables and the hardware failures. FIG. 8 shows an example of a correlation matrix, correlating hardware failures HW1, HW2, HW3, . . . HW10 to variables a, b, c, d, e, f, g, h, k, m, o, p, q, r, s. For example, hardware failure HW2 is uniquely correlated with variable b. For example, hardware failure HW7 is uniquely correlated with the combination of variables e, p, q. For example hardware failure HW6 does not correlate with any variable, and thus cannot be detected with the set of variables a, b, c, d, e, f, g, h, k, m, o, p, q, r, s.

The comparator 12 can store the correlation matrix and/or retrieve the correlation matrix from a memory. As already explained, preferably each hardware failure corresponds to a unique combination of one or more variables. Hence it is possible to uniquely identify a hardware failure from deviations in measured values of the variables. Herein a hardware failure can also be a degradation that is representative of an imminent breakdown, or indicative of a desired servicing or replacement. Thus, the device 1 can determine in step 106 a hardware degradation of a hardware component of the radiation therapy system on the basis of the determined average of the normalized value for one or more of the quantities, and on the basis of the unique correlation.

The correlation matrix can be produced manually, e.g. according to knowledge of the system. It is also possible, however, that the correlation matrix is generated, or updated, automatically. Thereto, each time a hardware failure is observed, variables that have recently changed can automatically be searched for. The device 1 can including a correlation unit 14. The correlation unit 14 is arranged for receiving data representative of hardware degradation of one or more hardware components of the radiation therapy system, and for determining a unique correlation between hardware degradation of a specific hardware component and a deviation in the determined average of the normalized value for one or more quantities.

According to an aspect the device 1 can be a distributed device arranged for monitoring a radiation therapy system 2 from a remote location. Alternatively, or additionally, the device can be arranged for detecting hardware degradation in a plurality of, e.g. mutually geographically remote, radiation therapy systems. In an example the device 1 is located at a central monitoring station arranged for monitoring a plurality of radiation therapy systems across a city, state, country, continent, or the world.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

While time appears to be the natural quantity to study drifts to the system, some other abscissa can be more relevant from a physics point of view. For instance, the aging of an ionization chamber is expected to be related to the cumulative dose it has received and the aging of a modulation wheel is expected to depend on the total number of cycles. Therefore any monotonous quantity can be used as abscissa, while the method remains valid by replacing time by the alternative quantity.

It will be appreciated that the device, or parts thereof, such as the measurement unit, normalizer, averaging unit, comparator, correlation unit, and/or communications unit can be embodied as dedicated electronic circuits, possibly including software code portions. The device, or parts thereof, such as the measurement unit, normalizer, averaging unit, comparator, correlation unit, and/or communications unit can also be embodied as software code portions executed on, and e.g. stored in, a memory of, a programmable apparatus such as a computer.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A method for detecting hardware degradation in a radiation therapy system delivering a plurality of fractions for a plurality of radiation fields, the method including the steps of:
   measuring, for each fraction of the plurality of radiation fields, a value for one or more quantities representative of a functioning of one or more hardware components of the system;
   normalizing, for each of the one or more quantities, the measured values;
   determining, for each of the one or more quantities, an average of the normalized values; and
   comparing, for each of the one or more quantities, the average of the normalized values with a respective predetermined value.

2. The method of claim 1, wherein the step of normalizing includes, for each of the one or more quantities, taking into account values measured for that quantity during delivery of previous fractions.

3. The method of claim 1, including:
   storing in a memory, for each of the one or more quantities, the determined average of the normalized values at subsequent points in time.

4. The method of claim 3, including the steps of:
   storing in the memory data representative of hardware degradation of one or more hardware components of the radiation therapy system, and
   determining a unique correlation between hardware degradation of a selected hardware component and a deviation in the determined average of the normalized value for one or more quantities.

5. The method of claim 1, wherein the normalizing includes, for each of the one or more quantities, normalizing the measured value with respect to previous values of the quantity measured during delivery of previous fractions.

6. The method of claim 1, further comprising monitoring the respective averages of the normalized values over a period of time.

7. The method of claim 1, further comprising determining, for each of the one or more quantities, whether the average of the normalized values displays a deviation from nominal behavior.

8. The method of claim 1, further comprising determining the respective predetermined value on the basis of a time development of the averages of the normalized values.

9. The method of claim 1, wherein the one or more quantities are one or more of beam position, noise level in an ionization chamber, or modulation wheel fluctuations.

10. A non-transitory computer-readable storage medium for detecting hardware degradation in a radiation therapy system arranged for delivering a plurality of fractions for a plurality of radiation fields, including instructions that, when executed by at least one processor, cause the at least one processor to perform steps comprising:
    receiving, for each fraction of the plurality of radiation fields, a measured value for one or more quantities representative of a functioning of one or more hardware components of the system;
    normalizing, for each of the one or more quantities, the measured values;
    determining, for each of the one or more quantities, an average of the normalized values; and
    comparing, for each of the one or more quantities, the average of the normalized values with a respective predetermined value.

11. The medium of claim 10, wherein the step of normalizing includes, for each of the one or more quantities, taking into account values measured for that quantity during delivery of previous fractions.

12. The medium of claim 10, wherein the normalizing includes, for each of the one or more quantities, normalizing the measured value with respect to previous values of the quantity measured during delivery of previous fractions.

13. The medium of claim 10, wherein the steps further comprise monitoring the respective averages of the normalized values over a period of time.

14. The medium of claim 10, wherein the steps further comprise determining, for each of the one or more quantities, whether the average of the normalized values displays a deviation from nominal behavior.

15. The medium of claim 10, wherein the instructions further comprise determining the respective predetermined value on the basis of a time development of the averages of the normalized values.

16. The medium of claim 10, wherein the one or more quantities are one or more of beam position, noise level in an ionization chamber, or modulation wheel fluctuations.

17. The medium of claim 10, wherein the steps further comprise:
    storing in a memory, for each of the one or more quantities, the determined average of the normalized values at subsequent points in time.

18. The medium of claim 17, wherein the steps further comprise:
    storing in the memory data representative of hardware degradation of one or more hardware components of the radiation therapy system, and
    determining a unique correlation between hardware degradation of a selected hardware component and a deviation in the determined average of the normalized value for one or more quantities.

* * * * *